US00PP33447P3

(12) United States Plant Patent
Diego

(10) Patent No.: US PP33,447 P3
(45) Date of Patent: Sep. 7, 2021

(54) ***RUBUS* PLANT NAMED 'BT RASTWO'**

(50) Latin Name: *Rubus ideaus*
Varietal Denomination: BT RASTWO

(71) Applicant: Berryplant di Grisenti Maria Maddalena & C. Societa Semplice Agricola, Baselga di Pine (IT)

(72) Inventor: Ioriatti Diego, Baselga di Pine (IT)

( * ) Notice: Subject to any disclaimer, the term of this patent is extended or adjusted under 35 U.S.C. 154(b) by 0 days.

(21) Appl. No.: 16/921,337

(22) Filed: Jul. 6, 2020

(65) Prior Publication Data

US 2021/0029859 P1 Jan. 28, 2021

(30) Foreign Application Priority Data

Jul. 23, 2019 (QZ) ..... PBR 2019/1765

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204, 203
CPC ..... A01H 5/0887
See application file for complete search history.

*Primary Examiner* — Kent L Bell

(57) ABSTRACT

A new and distinct cultivar of *Rubus* plant named 'BT RASTWO' is disclosed, characterized by very good tolerance to raspberry mite (*T. uticae*), yellow raspberry rust (*P. rubi-idae*) and resistant to frost damage. Plants produce many root suckers and very small, sparse spines. Fruit is broad-conical in shape, and colored light red, maintaining this light color during post-harvest. Plants fruit on both previous year's cane (mid-season) and current year's cane (mid to late season). The new variety is a *Rubus*, normally produced as an outdoor garden or container plant.

3 Drawing Sheets

Latin name of the genus and species: *Rubus ideaus*.
Variety denomination: 'BT RASTWO'.

BACKGROUND OF THE INVENTION

The new *Rubus* cultivar is a product of a planned breeding program conducted by the inventor in Baselgia di Pine, Italy. The objective of the breeding program was to produce new *Rubus ideaus* varieties for commercial applications. The cross resulting in this new variety was made during September of 2014.

The seed parent is the, unpatented variety referred to as *Rubus* 'BP15REG'. The pollen parent is the unpatented variety *Rubus* 'BP15BPW'. The new variety was selected July of 2016 by the inventor in a group of seedlings resulting from the 2014 crossing, in a research greenhouse in Baselgia di Pine, Italy.

Asexual reproduction of the new cultivar was performed by vegetative terminal cuttings. This was first performed at a research greenhouse in Baselgia di Pine, Italy during 2016 and has shown that the unique features of this cultivar are stable and reproduced true to type in multiple successive generations.

SUMMARY OF THE INVENTION

The cultivar 'BT RASTWO' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BT RASTWO'. These characteristics in combination distinguish 'BT RASTWO' as a new and distinct *Rubus* cultivar:

1. Very small spines.
2. Sparse spines.
3. Very good tolerance to raspberry mite, *T. uticae*.
4. Very good tolerance to yellow raspberry rust, *P. rubi-idae*.
5. Fruit slow to darken during post-harvest.
6. Many root suckers.
7. Good resistance to frost damage.
8. Fruit begins to be ripe medium to late season on current season's cane.
9. Fruit begins to be ripe medium season on previous season's cane.
10. Fruiting on previous year's cane in Summer.
11. Fruit on current year's cane in Fall.
12. Light red fruit color.
13. Broad conical fruit shape.

PARENT COMPARISON

Plants of the new cultivar 'BT RASTWO' are similar to plants of the seed parent, in most horticultural characteristics, however, plants of the new cultivar 'BT RASTWO' produce about 10 days later on primocane than the seed parent.

Plants of the new cultivar 'BT RASTWO' are similar to plants of the pollen parent, in most horticultural characteristics, however, plants of the new cultivar 'BT RASTWO' produce about 1 to 2 weeks later on primocane than the pollen parent.

COMMERCIAL COMPARISON

Plants of the new cultivar 'BT RASTWO' are comparable to the variety *Rubus* 'Advabertwee', U.S. Plant Pat. No.

23,914. The two *Rubus* varieties are similar in most horticultural characteristics, however, the new variety 'BT RASTWO' differs in the following:

1. The new variety 'BT RASTWO' produces many root suckers, 'Advabertwee' produces few root suckers.
2. Plants of the new variety have good resistance to frost damage, plants of this comparator have low to medium tolerance to frost damage.

Plants of the new cultivar 'BT RASTWO' can also be compared to the commercial variety *Rubus* 'Polka' (unpatented). These varieties are similar in most horticultural characteristics however, the new variety 'BT RASTWO' differs in the following:

1. Fruit of the new variety is lighter in color than fruit of 'Polka'.
2. Production begins about 15 to 20 days later on plants of the new variety compared to plants of 'Polka'.

BRIEF DESCRIPTION OF THE PHOTOGRAPHS

The photographs were taken using conventional techniques and although colors may appear different from actual colors due to light reflectance it is as accurate as possible by conventional photographic techniques. Colors in the photographs may appear to differ slightly from the color values cited in the botanical description, which accurately describe the colors.

DETAILED BOTANICAL DESCRIPTION

Figure 1:
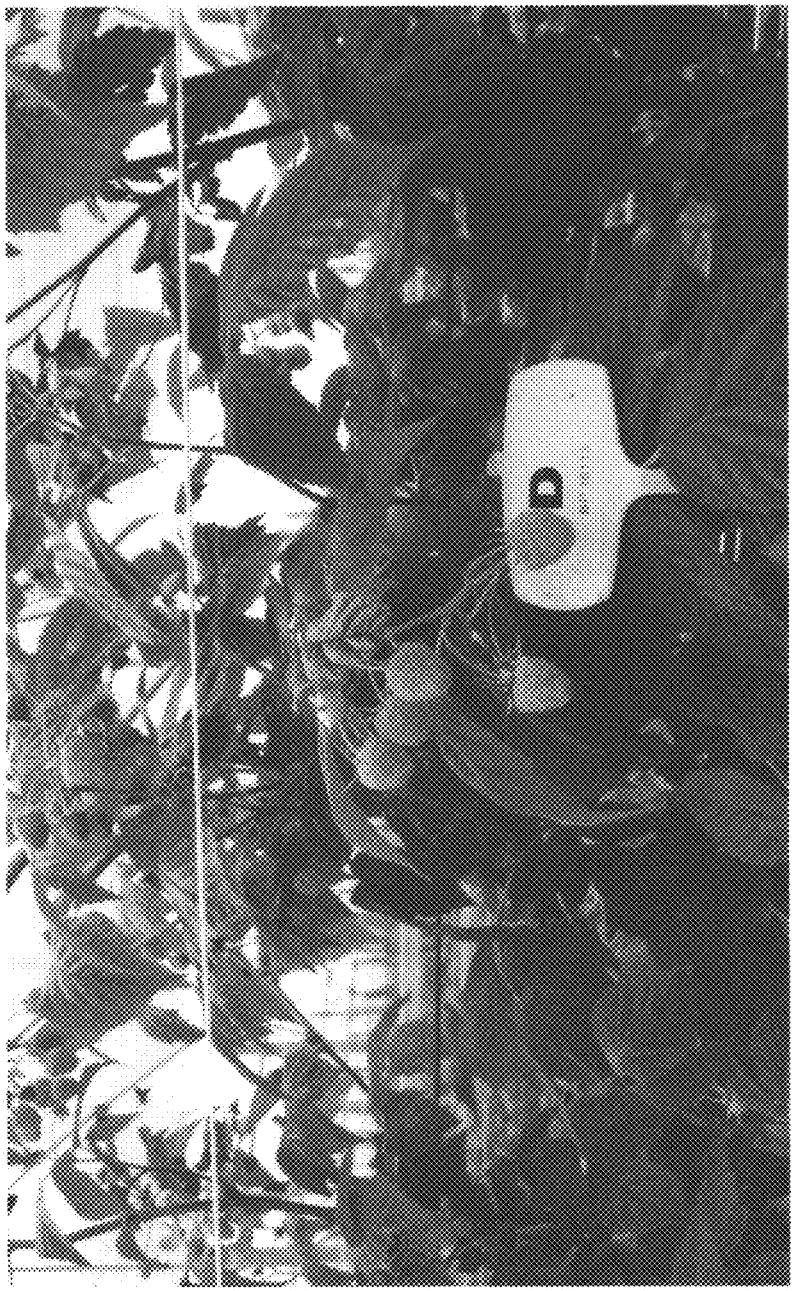
FIG. 1 illustrates in full color fruit and foliage on a plant of 'BT RASTWO'. Age of the plant is approximately 2 years grown in a poly hoop house.
Figure 2:
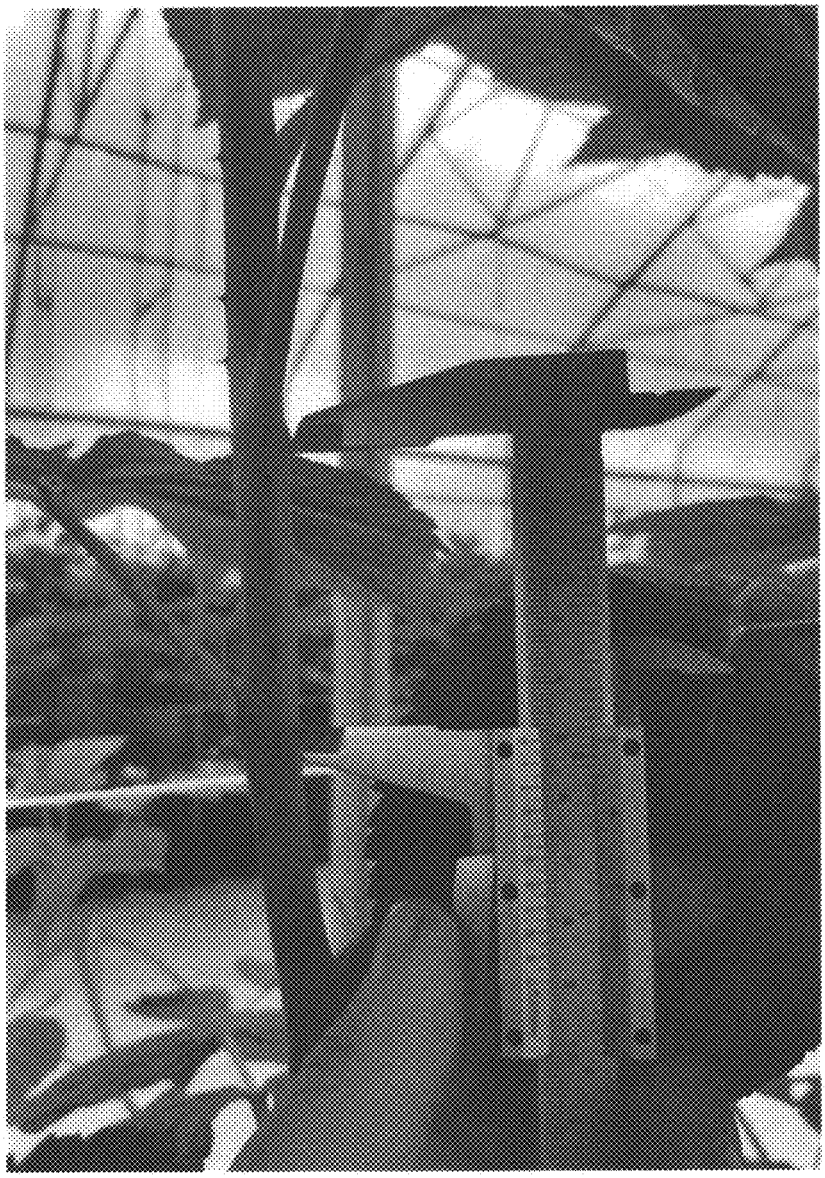
FIG. 2 illustrates in full color a typical stem and spines of the new variety.
Figure 3:
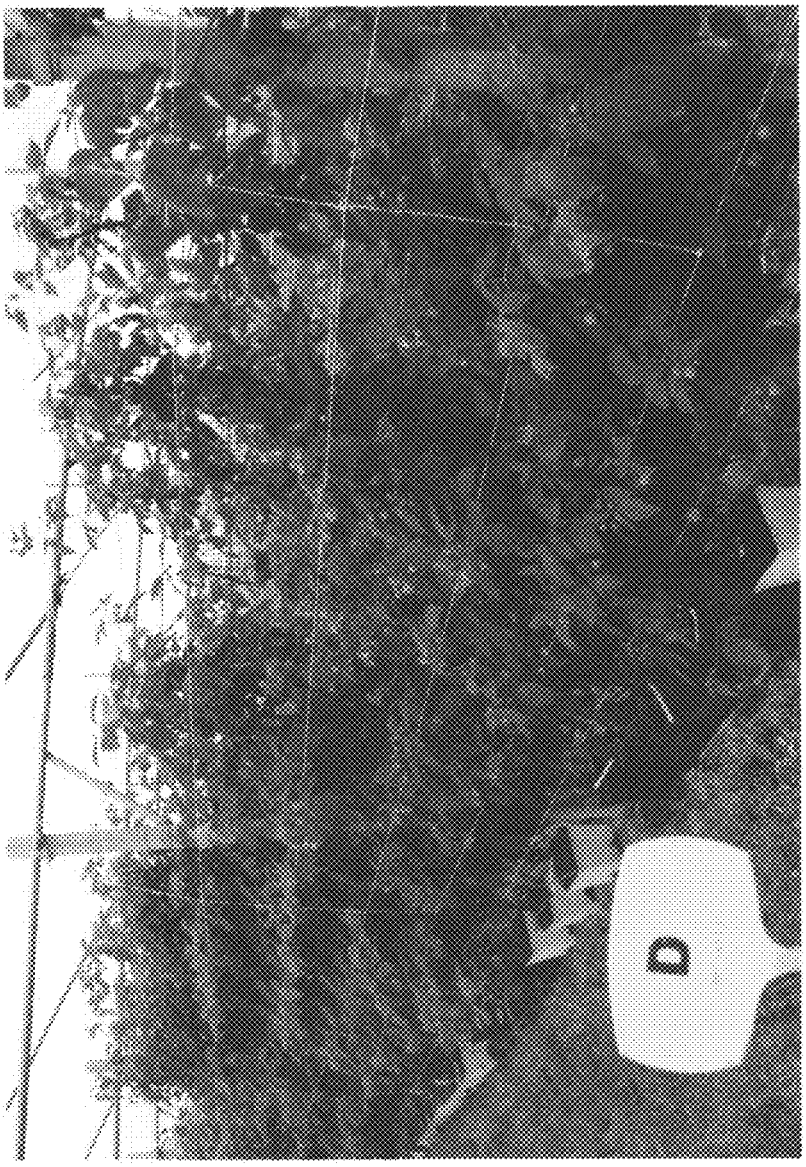
FIG. 3 illustrates in full color a row of typical plants of the new variety.

In the following description, color references are made to The Royal Horticultural Society Colour Chart 2007 except where general terms of ordinary dictionary significance are used. The following observations and measurements describe 'BT RASTWO' plants which were grown in Verona, Italy. Plants were grown in a season tunnel, given approximately 30% shading during Summer. The growing temperature ranged from about 15° C. to 34° C. during the day and from about 8° C. to 22° C. during the night. Measurements and numerical values represent averages of typical plant types. The description was made in June of 2020.

Botanical classification: *Rubus ideaus* 'BT RASTWO'.

PROPAGATION

Time to initiate roots: About 35 days at approximately 16° C.

Time to produce a rooted cutting: About 45 days at 18° C.

PLANT

Age of plant described: About 1 year.
Plant spread: Approximately 210 cm.
Plant height: Approximately 70 cm.
Habit: Semi-upright.
Primocane length: Approx. 200 cm.
Primocane color: Near RHS Yellow-Green N144C.
Anthocyanin coloration present: Not typical.
Dormant cane color: Near RHS Greyed-Orange 177A.
Primocane diameter: Average 12 cm.
Internode length: Average 6.5 cm.
Spines:
- *Approximately density/quantity of spines.*—Approximately 1 per 2 to 3 cm of stem length.
- *Length.*—Average range 2.5 to 3.5 mm.
- *Color.*—Near RHS Greyed-Purple N186C.
- *Shape.*—Short deltate.

Fruiting laterals:
- *Length.*—40-50 cm.
- *Texture.*—Minutely spined, moderately dense.
- *Color.*—Near RHS Yellow-Green 144B.
- *Aspect.*—Semi-erect.

FOLIAGE

Leaf:
- *Arrangement.*—Compound opposite.
- *Quantity.*—9-10 per stem.
- *Average length.*—Approximately 24 cm.
- *Average width.*—Approximately 22 cm.

Leaflet:
- *Quantity.*—Most common quantity of leaflets per leaf: 3.
- *Average length.*—Approximately 11-14 cm.
- *Average width.*—Approximately 9-12 cm.
- *Shape of blade.*—Overall broad deltate.
- *Apex.*—Apiculate.
- *Base.*—Ovate.
- *Margin.*—Double serrate.
- *Texture of top surface.*—Coriaceous.
- *Texture of bottom surface.*—Coriaceous.
- *Pubescence.*—Ver little.
- *Leaf internode length.*—5-7 cm.
- *Color.*—Young foliage upper side: Near RHS Yellow-Green 144A. Young foliage under side: Near RHS Green 142B. Mature foliage upper side: Near RHS Green 141A. Mature foliage under side: Near RHS Green 135C.
- *Venation.*—Type: Cross veniculate, pinnate along main axis. Venation color upper side: Near Yellow-Green 144C. Venation color under side: Near Yellow-Green 144D.
- *Petiole.*—Length: 5 cm. Width: 3 mm. Color: Near RHS Yellow-Green N144C. Texture: Glabrous.
- *Rachis.*—Length: 12-13 cm. Width: 3-4 mm. Color: Near RHS Yellow-Green N144C. Texture: Glabrous.
- *Stipules.*—Not observed.

FLOWER

Flowering season: Begins around August 15 in Verona, Italy.
Inflorescence:
- *Flowers per.*—18-30.

Flower size:
- *Diameter.*—Approximately 2.5 cm.
- *Length.*—Approximately 1.2 cm.

Peduncle:
- *Length.*—5 cm.
- *Diameter.*—0.2 cm.
- *Color.*—Near RHS Yellow-Green N144C.
- *Texture.*—Glabrous.

Pedicel:
- *Length.*—1.3 cm.
- *Diameter.*—0.2 cm.

*Color*.—Near RHS Yellow-Green N144C.
*Texture*.—Glabrous.

Petals:
*Petal arrangement*.—Rotate.
*Length*.—0.9 cm.
*Width*.—0.5 cm.
*Shape*.—Semi-cuneate.
*Margin*.—Entire.
*Apex*.—Rounded.
*Base*.—Rounded.
*Petal quantity*.—5.
*Texture*.—Glabrous.

Color:
*Petals*.—When opening: Upper surface: Near RHS White N155B. Lower surface: Near RHS White N155B. Fully opened: Upper surface: Near RHS White N155B. Lower surface: Near RHS White N155B.

Bud:
*Shape*.—Ovate.
*Length*.—Approximately 0.8 cm.
*Diameter*.—Approximately 0.4 cm.
*Color*.—Near RHS Greyed-Orange 166A.

Sepals:
*Length*.—1.5 cm.
*Width*.—0.6 cm.
*Shape*.—Narrow deltate with apiculate apex.
*Color*.—Interior Surface: Near RHS Green 140C. Exterior Surface: Near RHS Green 141B.
*Texture*.—Glabrous.

REPRODUCTIVE ORGANS

Androecium:

Stamens:
*Number*.—130.
*Filament length*.—Approximately 6 mm.
*Filament color*.—Near RHS Green-White 157A.

Anthers:
*Length*.—0.8 mm.
*Shape*.—Ovate.
*Color*.—Near RHS Greyed-Orange 164A.
*Pollen*.—Quantity: Abundant. Color: Near RHS White N155C.

Pistil:
*Number*.—120.
*Length*.—Approximately 4 mm.
*Style*.—Length: Approximately 0.4 cm. Color: Near RHS Green-White 157A.

FRUIT

Market use: Fresh consumption.
Length: 4.5 cm.
Diameter: 3 cm.
General shape in lateral view: Broad-conical.
Color: Near RHS Red 44C to 44D.
Average druplets per berry: 150-190.
Druplet shape and size: Round-conical, about 3 to 4 mm long and 2 to 3 mm wide.
Average weight per berry: 6 grams.
Fruit brix: Average 11%.
Fruit bearing on floricane/primocane or both: Both.
Fruit begins ripening: Primocane about August $20^{th}$, floricane about April $20^{th}$.
Fruiting season: Primocane September to mid-October, floricane June to mid-July.
Yield per hectare: 20 ton/ha in primocane, 20 ton/ha in floricane.
Other fruit characteristics: Very stable clear color also maintained after harvest. Color maintained for approximately 1 week at 4° C.

OTHER CHARACTERISTICS

Disease/pest resistance: Very good tolerance to raspberry mite, *T. uticae*. Also observed good tolerance to yellow raspberry rust, *P. rubi-idae*.
Temperature tolerance: Maximum 36° C. during pollination and harvest. Good tolerance to winter frosts to −15° C.

What is claimed is:

1. A new and distinct cultivar of *Rubus* plant named 'BT RASTWO' as herein illustrated and described.

* * * * *